United States Patent
Blaine

[11] Patent Number: 6,113,261
[45] Date of Patent: Sep. 5, 2000

[54] METHOD AND APPARATUS OF MODULATED-TEMPERATURE THERMOGRAVIMETRY

[75] Inventor: Roger L. Blaine, New Castle, Del.

[73] Assignee: TA Instruments, Inc., New Castle, Del.

[21] Appl. No.: 09/105,238

[22] Filed: Jun. 26, 1998

Related U.S. Application Data

[60] Provisional application No. 60/051,169, Jun. 27, 1997.

[51] Int. Cl.[7] ............................. G01G 23/00; G01N 25/00
[52] U.S. Cl. .............................................................. 374/14
[58] Field of Search .................................. 374/14, 55, 56, 374/10; 177/150, 245

[56] References Cited

U.S. PATENT DOCUMENTS

| | | | |
|---|---|---|---|
| 4,606,649 | 8/1986 | Mikhail ..................................... | 374/14 |
| 4,693,252 | 9/1987 | Thoma et al. ........................... | 128/400 |
| 4,817,745 | 4/1989 | Beshoory ................................. | 374/14 |
| 4,848,093 | 7/1989 | Simmonds et al. ..................... | 62/49.1 |
| 4,871,961 | 10/1989 | Kersten et al. ........................ | 323/267 |
| 5,165,792 | 11/1992 | Crowe et al. ............................ | 374/14 |
| 5,215,377 | 6/1993 | Sugano .................................... | 374/14 |
| 5,224,775 | 7/1993 | Reading et al. ......................... | 374/11 |
| 5,306,087 | 4/1994 | Nakamura et al. ..................... | 374/14 |
| 5,368,391 | 11/1994 | Crowe et al. ............................ | 374/14 |
| 5,466,066 | 11/1995 | Hidaka .................................... | 374/14 |
| 5,826,983 | 10/1998 | Nakamura et al. ..................... | 374/14 |

FOREIGN PATENT DOCUMENTS

| | | |
|---|---|---|
| 33 04 322 A1 | 8/1984 | Germany . |
| 43 36 973 A1 | 4/1995 | Germany . |
| 195 04 470 A1 | 8/1996 | Germany . |

*Primary Examiner*—G. Bradley Bennett
*Assistant Examiner*—Gail Verbitsky
*Attorney, Agent, or Firm*—Shaw Pittman

[57] ABSTRACT

A method for controlling a thermogravimetry experiment and for quantitatively determining kinetic constants for decomposition or volatilization reactions using periodic forcing (modulated) temperature functions. A temperature program having a linear part and a periodically varying part superimposed thereon is applied to a sample in a thermogravimetric analyzer. The resulting mass signal is deconvoluted, or separated, into one or more deconvoluted signals.

81 Claims, 3 Drawing Sheets

METHOD AND APPARATUS OF MODULATED-TEMPERATURE THERMOGRAVIMETRY

The present application hereby claims benefit of the priorty date of U.S. Provisional Application No. 60/051,169, which was filed on Jun. 27, 1997.

FIELD OF THE INVENTION

The present invention relates to methods for controlling the temperature program used with thermogravimetric analyses.

BACKGROUND OF THE INVENTION

Kinetics is the study of the dependence of a chemical reaction on time and temperature. Kinetic reactions are often described using two equations. The first of these is known as the rate equation and describes the relationship between the rate of reaction, time and amount of material. For homogeneous decomposition or volatilization reactions, the reaction is almost universally found to follow the general rate equation which takes the form:

$$\frac{d\alpha}{dt} = k(T)[f(\alpha)]^n \quad (1)$$

Where:
- $\alpha$=reaction fraction
- $d\alpha/dt$=rate of reaction
- $k(T)$=rate constant at a given temperature T
- T=absolute temperature
- $f(\alpha)$=kinetic expression
- n=reaction order The second equation describing kinetic reactions details the dependence of the rate constant on temperature and is known as the Arrhenius equation.

$$k(T) = Ze^{(-E/RT)} \quad (2)$$

Where:
- Z=the pre-exponential factor
- e=natural logarithm base
- E=activation energy
- R=gas constant The rate and Arrhenius equations may be combined into a single form:

$$\frac{d\alpha}{dt} = Z[f(\alpha)]^n e^{(-E/RT)} \quad (3)$$

The parameters E, Z and n are called kinetic constants and may be used to model the dependence of a chemical reaction on time and temperature.

Thermogravimetry is used to obtain kinetic constants of decomposition or volatilization reactions using one of several common methods. One approach is known as the "factor jump" method where the temperature of the test specimen is "stepped" between two or more isothermally held temperatures in the weight loss region. The rate of weight loss ($d\alpha/dt$) at each of the isothermal regions may be substituted into equation (3), along with the respective isothermal temperature(T). Any two equations for adjacent steps may then be examined as their ratio and the resultant form may be solved for activation energy.

$$E = \frac{RT_1 T_2}{T_1 - T_2} \left[ \ln \frac{d\alpha_1}{d\alpha_2} + \ln \frac{f(\alpha_2)}{f(\alpha_1)} \right] \quad (4)$$

Where:
- $d\alpha_1$=rate of weight loss at temperature $T_1$
- $d\alpha_2$=rate of weight loss at temperature $T_2$
- $f(\alpha_1)$=kinetic expression at the value of $d\alpha_1$
- $f(\alpha_2)$=kinetic expression at the value of $d\alpha_2$ Should the values for $d\alpha_1$ and $d\alpha_2$ be extrapolated to a common conversion level, then $\alpha_1=\alpha_2$ and $\ln[f(\alpha_1)/f(\alpha_2)]=0$, reducing equation (4) to a more easily evaluated form:

$$E = \frac{RT_1 T_2 \ln(d\alpha_1/d\alpha_s)}{T_1 - T_2} \quad (5)$$

SUMMARY OF THE INVENTION

In thermal analysis, the temperature rate of change is a forcing function (or independent parameter) which produces some physical or chemical change in a test specimen resulting in a measured response (or dependent experimental) parameter such as weight change. A linear temperature ramp is the most commonly used of these forcing functions. U.S. Pat. No. 5,224,775, which is incorporated by reference herein, however, introduced to thermal analysis (including thermogravimetry), the concept of a modulated-temperature forcing function. In the modulated temperature approach, a linear temperature ramp is modulated with a sinusoidal heating rate oscillation. This periodic temperature function produces corresponding oscillatory output response signal proportional to some physical property of the material under test. Deconvolution of the resultant experimental parameter signals leads to analytical information unavailable from the linear ramp forcing function alone.

In this invention, a sinusoidal heating rate oscillation is applied to thermogravimetry to obtain dependent parameters signals useful for the obtaining of kinetic information. Specifically, if the temperature is changed in an sinusoidal fashion around an average temperature (T), then the values of the peak temperatures may be given (T+A) and (T−A), where A is the half peak-to-peak amplitude. This forcing function produces a corresponding oscillatory rate of weight change and logarithm of the rate of weight change response signals. These terms may be substituted into equation (4) to obtain:

$$E = \frac{R(T^2 - A^2)}{2A} \left[ \ln \frac{d\alpha_1}{d\alpha_2} + \ln \frac{f(\alpha_2)}{f(\alpha_1)} \right] \quad (6)$$

A mathematical deconvolution technique, such as a discrete fast Fourier transformation, may be applied to the forcing and response functions to obtain average and amplitude values on a continuous bases. If average temperature oscillation (T), temperature amplitude (2A), rate of weight loss ($d\alpha/dt$) and amplitude of the logarithm of rate of weight loss $[L=\ln(d\alpha_1/d\alpha_2)]$ are obtained for constant conversation values [i.e., $\alpha_1=\alpha_2$ and $\ln[f(\alpha_1)/f(\alpha_2)=0]$, equation (6) reduces to:

$$E = \frac{R(T^2 - A^2)L}{2A} \quad (7)$$

This equation is independent of the form of the reaction equation and may be said to be model independent. If, however, a model is selected then other kinetic parameters, such as the pre-exponential factor and reaction order, may be obtained. Homogeneous decomposition or volatilization reactions are almost universally found to follow first order kinetics where n=1 and the logarithm of the pre-exponential factor equals ln $[d\alpha/(1-\alpha)]+E/RT$.

The use of continuously deconvoluted, or separated, values of the oscillatory forcing functions and corresponding oscillatory response provides, then, for the continuous generation of activation energy and pre-exponential factor throughout the reaction range.

Further, U.S. Pat. No. 5,165,792, which is incorporated by reference herein, describes how the heating rate (temperature forcing function) in thermal analysis may be adjusted according to the rate of change of a dependent parameter. In thermogravimetry, the temperature of the experiment is adjusted to maintain an average rate of weight change. A second part of this invention involves the control of the average experimental temperature using the average rate of weight change generated by the deconvolution.

According to equation (1), the rate of the reaction will decrease as the amount of reactant is consumed. To compensate for this rate of weight change reduction, the average temperature is adjusted during the reaction according to the average rate of weight change obtained from the deconvoluted response signal. This provides a smooth, continuous, and rapid change in the average temperature during regions where no weight change is observed but then a decrease in the average temperature change rate where weight changes reaction occur. Once a weight change is complete, the average temperature of the modulated temperature experiment is automatically increased until another weight change region is observed or the maximum temperature of the experiment is reached.

DETAILED DESCRIPTION OF THE INVENTION

Figure 1:
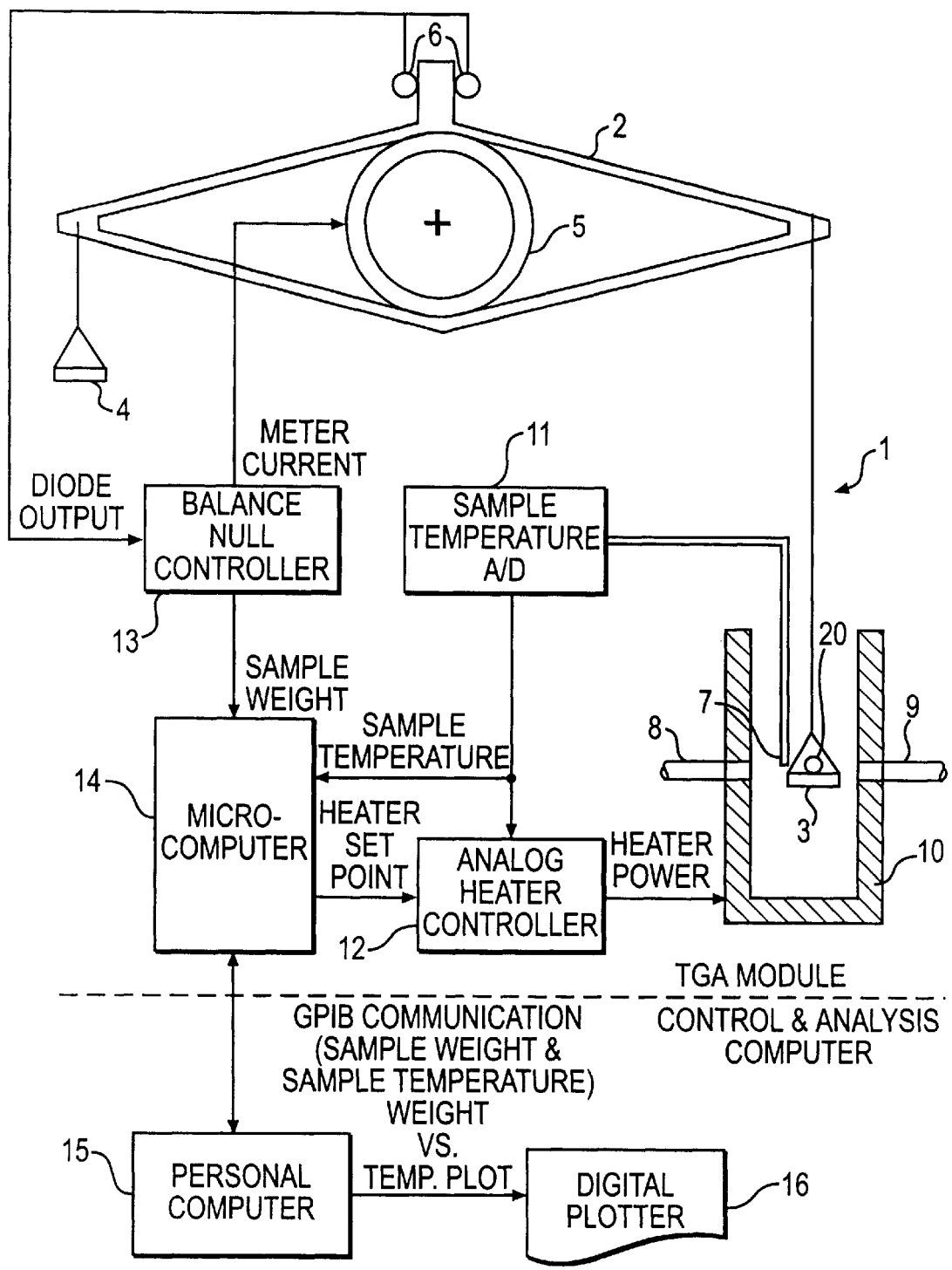
FIG. 1 illustrates schematically a thermogravimetric analyzer for use in the present invention.

FIG. 1 is a schematic illustration of a thermogravimetric analyzer (TGA) for that can be used with the present invention. TGAs are well known in the art, and will be described only in a overview sense herein. An example TGA for use in the present invention is the TGA 2950 from TA Instruments, Inc. of New Castle, Del. A more detailed description can be found in U.S. Pat. No. 5,165,792, which is hereby incorporated in its entirety, and in U.S. Pat. No. 5,368,391, which is hereby incorporated by reference in its entirety. A sample 20 is placed at a sample position 3 in the TGA. Elements 1–6 comprise an electrobalance in which a sample at position 3 is balanced by a counterbalance 4 and a torque motor 5. As sample 20 loses weight, the force on torque motor 5 is changed so that the system remains in balance. The signal to torque motor 5 is proportional to the mass remaining of the sample.

The sample is surrounded by a furnace, or oven, composed of elements 7–10. The temperature of the furnace is controlled by a heater controller 12. Control is preferably performed using a feed back control system comprising a temperature sensor 7 and a heater set point generated by a microcomputer 14. That is, microcomputer 14 calls for the furnace to be at a particular temperature. The actual furnace temperature is determine by temperature sensor 7. Heater controller 12 provides power to the furnace so that the difference between the set point and the actual temperature approaches zero.

The temperature of the sample determined by temperature sensor 7, and the weight information provided by the electrobalance, determined by a balance null controller 13, are the primary signals generated by the TGA. These signals are preferably treated further by a computer 15 to obtain other information such as rates of change of mass. These additional signals can be fed back to the microcomputer to help generate the desired temperature program. A more detailed description of FIG. 1 is given in U.S. Pat. No. 5,165,792 at column 7, lines 9–46, and in U.S. Pat. No. 5,368,391 at column 7, lines 10–50.

In the present invention the temperature program can be characterized as having a modulation period, a modulation amplitude and an underlying heating or cooling rate. Preferably, the temperature program has a linearly varying part onto which a periodically varying part is superimposed to created a "modulated" temperature program. The modulated temperature program has a modulation amplitude, modulation period or frequency and underlying heating or cooling rate. Appropriate signals for the periodically varying part include, but are not limited to, a triangle wave, a square wave, a sinusoidal wave and a saw tooth wave or any combination thereof.

The temperature program can be selected in a variety of ways. Preferably, the modulation amplitude, modulation period or frequency and underlying heating or cooling rate are selected explicitly by the user. Similarly, a user can select parameters which microcomputer 14 of computer 15 then converts into a modulation amplitude, modulation frequency or period and underlying heating or cooling rate.

Preferably the linearly varying part and the periodically varying part are summed to form the temperature program of the present invention. The summation can be performed in a well-known manner using analog and/or digital components.

Figure 2:
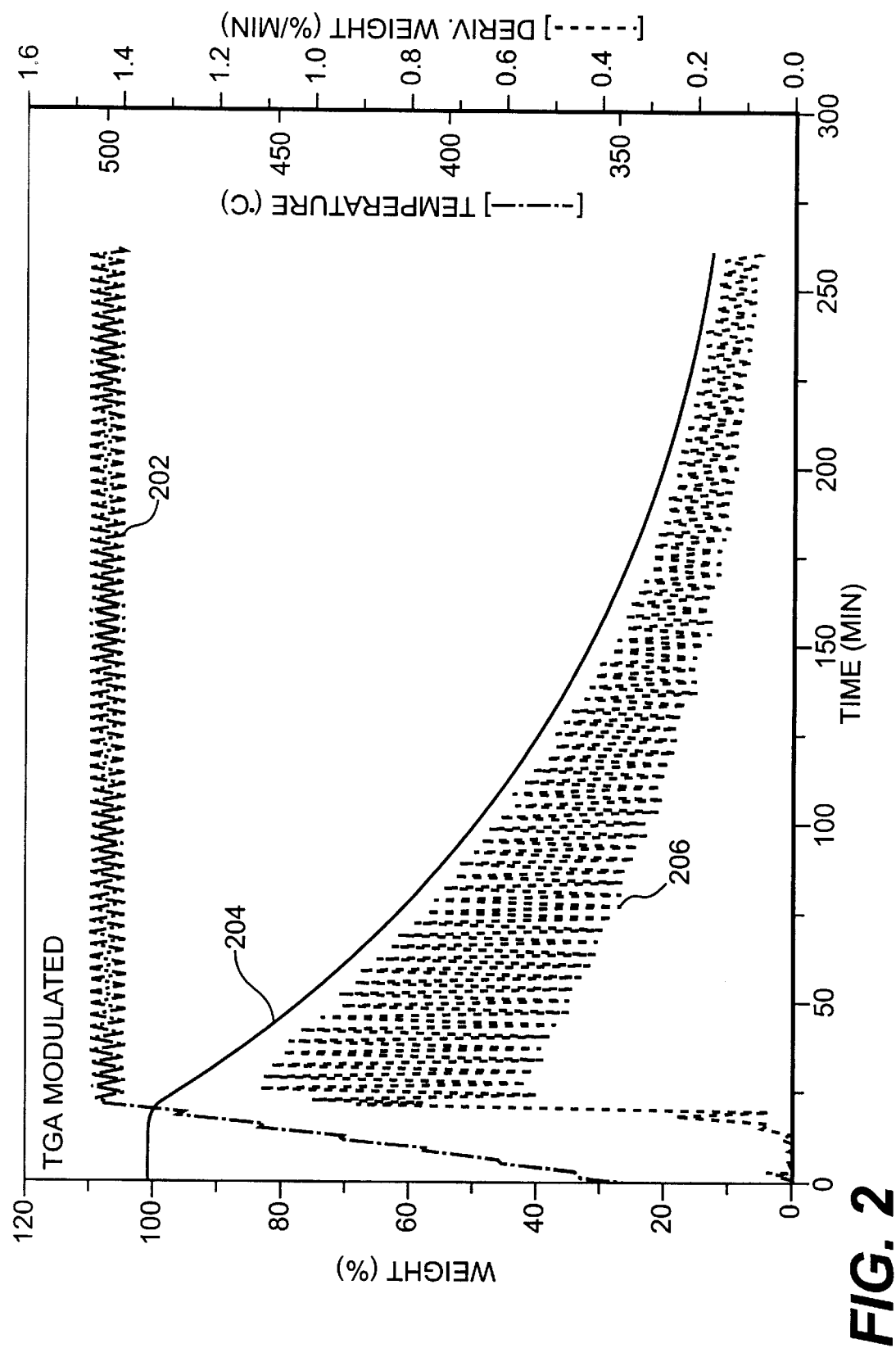
FIG. 2 is a plot showing the decomposition of poly (tetrafluoroethylene) using quasi-isothermal temperature modulation.
Figure 3:
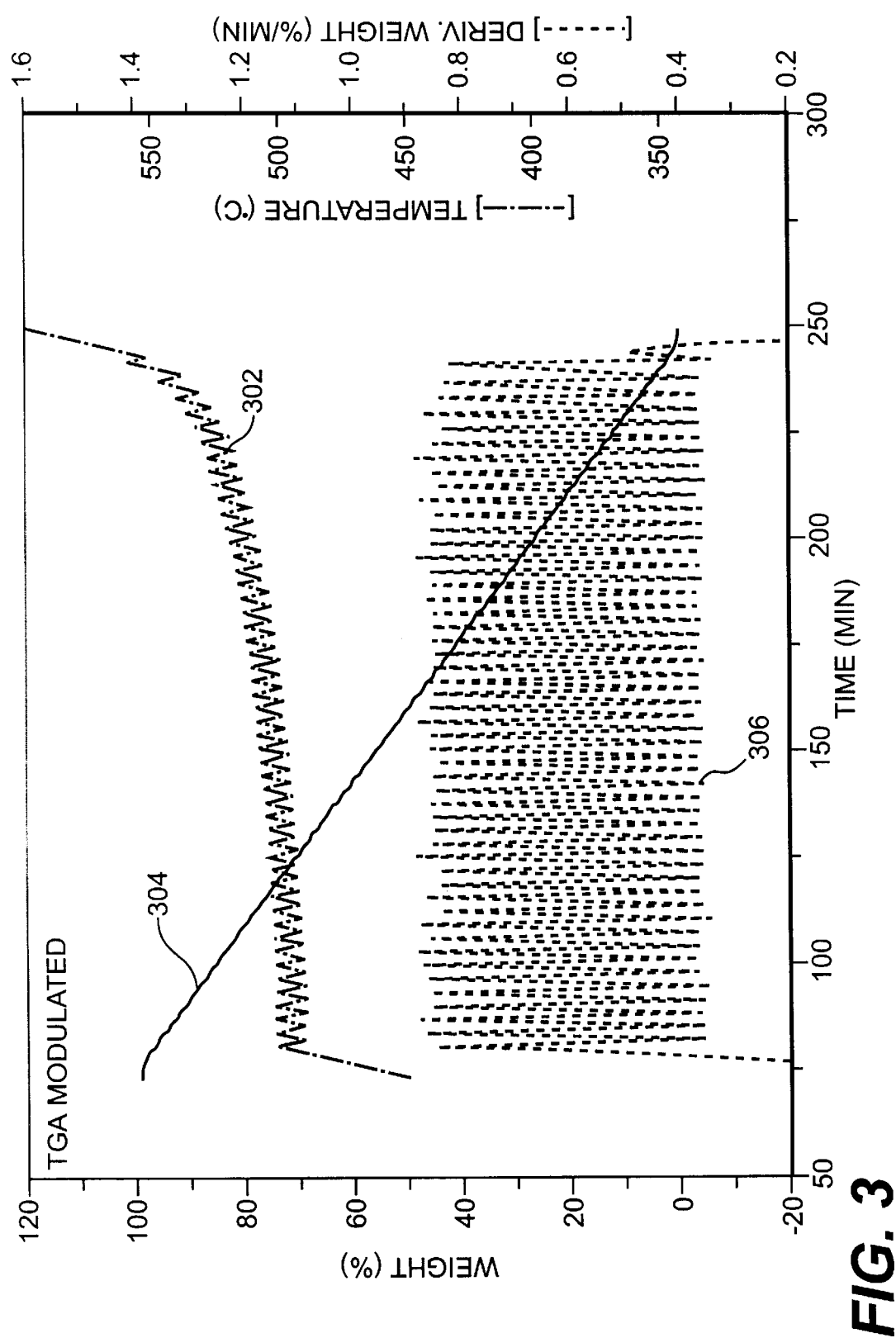
FIG. 3 is a plot showing the decomposition of poly (tetrafluoroethylene) using temperature modulation and constant average rate of weight loss.

The present invention is illustrated herein through the use of two examples. The results of the examples are shown in FIGS. 2 and 3. FIGS. 2 and 3 display three signals on the Y-axis as a function of time (the X-axis). In each Figure, the percent of the original weight of the sample is presented in the middle line, the temperature of the sample is shown in the upper line, and the rate of change of the percent original sample weight is presented in the lower line.

In the example shown in FIG. 2, the temperature was sinusoidally modulated with an amplitude of ±5° C. and a period of 200 seconds. This modulated temperature was superimposed over an underlying temperature ramp at 7° C./min, starting from ambient temperature up to 500° C./min and held there for approximately 200 minutes. The temperature program is shown as curve 202. Note that temperature program curve 202 can have an underlying heating rate or cooling rate of zero. At this quasi-isothermal region, the weight of the sample decreases in an exponential fashion from the 100% original weight to about 20%. The weight is shown as a percentage of the original weight in curve 204. The rate of weight loss is not smooth but has short term variation in response to the sinusoidal temperature oscillations as shown in the rate of weight change curve. The rate of weight loss in percent of original weight per minute is shown in curve 206. The average rate of weight loss and the amplitude of the oscillatory rate of weight loss are observed to decrease with increasing conversion (decreasing weight percent).

In the example shown in FIG. 3, the temperature was increased at 7° C./min until the rate of sample weight loss reaches 0.8%/min. Once the limit was reached, the temperature was cooled at 7° C./min until the rate of weight loss fell below 0.4%/min. This heat/cool cycle was repeated, producing a sawtooth temperature modulation of amplitude ±5° C. and a period of 200 seconds around an average temperature. The temperature program is illustrated as curve 302. Once the sample was consumed, the temperature was once again increased at a rate of 7° C. until another weight loss is observed or the temperature limit is reached. This approach produces a temperature program where the average temperature is controlled to maintain a constant average rate of weight loss. The weight of the sample as a percentage of original weight is shown in curve 304. The rate of weight loss as a percentage of the original weight per minute is shown in curve 306.

What is claimed is:

1. A thermogravimetric analyzer (TGA), comprising:
   a sample holder into which a sample to be analyzed is placed;
   means for selecting a temperature program that can be characterized by an amplitude, a modulation period or a modulation frequency and an underlying heating rate;
   an oven to vary the temperature of said sample according to said temperature program;
   means for obtaining a weight information signal indicative of weight information of said sample over time due to heating according to the temperature program;
   processor means for determining at least one kinetic parameter using said weight information signal.

2. The TGA of claim 1, wherein said temperature program comprises the sum of a linear part and a periodically varying part.

3. The TGA of claim 2, wherein said periodically varying part is one of a sine wave, a triangle wave, a square wave and a saw tooth wave.

4. The TGA of claim 1, wherein said underlying heating rate is zero.

5. A method for analyzing a sample, comprising the steps of:
   placing the sample in an oven;
   varying temperature of said sample according to a temperature program that can be characterized by a modulation amplitude, modulation period and an underlying heating rate;
   obtaining weight information of said sample over time as a weight information signal; and
   determining at least one kinetic parameter using said weight information signal.

6. The method of claim 5, further comprising the step of selecting said temperature program by selecting a linear part and a periodically changing part.

7. The method of claim 5, further comprising the steps of
   selecting parameters to define said temperature program; and
   converting said parameters into said modulation amplitude, said modulation frequency or period and said underlying heating rate.

8. The method of claim 5, further comprising the step of selecting said underlying heating rate to be zero.

9. The TGA recited in claim 1, wherein said weight information is one of a weight of said sample, a percentage of original weight of said sample, a rate of change of weight of said sample and a rate of change of original weight of said sample.

10. The TGA recited in claim 1, wherein said at least one kinetic parameter is at least one of an activation energy, a pre-exponential factor and a reaction order.

11. The TGA of claim 1, wherein said weight information signal is recorded.

12. The method recited in claim 5, wherein said step of obtaining weight information comprises the step of obtaining one of a weight of said sample, a percentage of original weight of said sample, a rate of change of weight of said sample and a rate of change of original weight of said sample.

13. The method recited in claim 5, wherein said step of determining at least one kinetic parameter comprises the step of determining one of an activation energy, a pre-exponential factor and a reaction order.

14. A thermogravimetric analyzer, comprising:
   a sample holder into which a sample is placed;
   an oven to heat the sample according to a temperature program that can be characterized by an amplitude and a period and an average temperature;
   an electrobalance to determine weight information of the sample as it is heated according to the temperature program; and
   a computer to obtain the weight information and determine at least one kinetic parameter based on the weight information.

15. The thermogravimetric analyzer recited in claim 14, wherein the at least one kinetic parameter is at least one of an activation energy, an exponential factor and a reaction order.

16. The thermogravimetric analyzer recited in claim 14, wherein the weight information is one of a weight of said sample, a percentage of original weight of said sample, a rate of change of weight of said sample and a rate of change of original weight of said sample.

17. The thermogravimetric analyzer recited in claim 14, further comprising a controller to adjust the temperature program in accordance with the determined kinetic parameter.

18. The thermogravimetric analyzer recited in claim 17, wherein the weight information is rate of weight change, and wherein the controller comprises a process to adjust the temperature program in accordance with an average rate of weight change calculated from the weight information signal.

19. The thermogravimetric analyzer recited in claim 17, wherein the controller comprises a process to adjust the temperature program to maintain a constant rate of weight change.

20. The thermogravimetric analyzer recited in claim 17, wherein the weight information is weight change, and wherein the controller comprises a process to adjust the temperature program in accordance with an average rate of weight change calculated from the weight information signal.

21. The thermogravimetric analyzer recited in claim 17, wherein the controller comprises a process to adjust the average temperature during a reaction occurring in the sample.

22. A method for analyzing a sample, comprising:
   placing the sample into a sample holder;
   heating the sample according to a temperature program that can be characterized by an amplitude, a period and an average temperature;
   determining weight information of the sample as it is heated according to the temperature program; and
   obtaining the weight information in computer; and
   using the computer to determine at least one kinetic parameter based on the weight information.

23. The method recited in claim 22, wherein the at least one kinetic parameter is at least one of an activation energy, an exponential factor and a reaction order.

24. The method recited in claim 22, wherein the weight information is one of a weight of said sample, a percentage of original weight of said sample, a rate of change of weight of said sample and a rate of change of original weight of said sample.

25. The method recited in claim 22, further comprising the step of adjusting the temperature program in accordance with the determined kinetic parameter.

26. The method recited in claim 25, wherein the weight information is rate of weight change, and wherein the adjusting step further comprises the step of adjusting the temperature program in accordance with an average rate of weight change calculated from the weight information signal.

27. The method recited in claim 25, further comprising the step of adjusting the temperature program to maintain a constant rate of weight change.

28. The method recited in claim 25, wherein the weight information is weight change, and wherein the adjusting step further comprises the step of adjusting the temperature program in accordance with an average rate of weight change calculated from the weight information signal.

29. The method recited in claim 25, wherein the adjusting step further comprises the step of adjusting the average temperature during a reaction occurring in the sample.

30. A thermogravimetric analyzer for analyzing a sample, comprising:
   a sample holder into which to place the sample;
   an oven for heating the sample according to a temperature program having at least one segment, wherein each segment can be characterized by a modulation amplitude and a modulation period;
   a balance to determine a weight information signal indicative of weight information of said sample as it is heated according to the temperature program; and
   a computer to determine a kinetic parameter using the weight information signal.

31. The thermogravimetric analyzer recited in claim 30, wherein said weight information is one of a weight of said sample, a percentage of original weight of said sample, a rate of change of weight of said sample and a rate of change of original weight of said sample.

32. The thermogravimetric analyzer recited in claim 30, wherein said kinetic parameter is at least one of an activation energy, a pre-exponential factor and a reaction order.

33. The thermogravimetric analyzer recited in claim 30, wherein each segment can further be characterized by an underlying heating rate.

34. The thermogravimetric analyzer recited in claim 30, wherein at least one particular segment can be characterized as having an underlying heating rate of zero.

35. The thermogravimetric analyzer recited in claim 30, wherein at least one particular segment can be characterized as having an underlying heating rate that varies over time.

36. The thermogravimetric analyzer recited in claim 35, wherein the variation of the underlying heating rate over time is based on the determined kinetic parameter.

37. The thermogravimetric analyzer recited in claim 30, wherein there is only one segment that can be characterized as having an underlying heating rate that varies over time.

38. The thermogravimetric analyzer recited in claim 37, wherein the variation of the underlying heating rate over time is based on the determined kinetic parameter.

39. A method for analyzing a sample, comprising:
   placing the sample in a sample holder;
   heating the sample according to a temperature program having at least one segment, wherein each segment can be characterized by a modulation amplitude and a modulation period;
   determining a weight information signal indicative of weight information of said sample as it is heated according to the temperature program; and
   determining a kinetic parameter using the weight information signal.

40. The method recited in claim 39, wherein said weight information is one of a weight of said sample, a percentage of original weight of said sample, a rate of change of weight of said sample and a rate of change of original weight of said sample.

41. The method recited in claim 39, wherein said kinetic parameter is at least one of an activation energy, a pre-exponential factor and a reaction order.

42. The method recited in claim 39, wherein said heating step comprises the step of heating the sample according to the temperature program, and wherein each segment can further be characterized by an underlying heating rate.

43. The method recited in claim 39, wherein said heating step comprises the step of heating the sample according to the temperature program, and wherein at least one particular segment can be characterized as having an underlying heating rate of zero.

44. The method recited in claim 37, wherein said heating step comprises the step of heating the sample according to the temperature program, and wherein the at least one particular segment can be characterized as having an underlying heating rate that varies over time.

45. The method recited in claim 44, further comprising the step of varying the underlying heating rate over time is based on the determined kinetic parameter.

46. The method recited in claim 39, wherein there is only one segment that can be characterized as having an underlying heating rate that varies over time.

47. The method recited in claim 46, further comprising the step of varying the underlying heating rate over time is based on the determined kinetic parameter.

48. A system for analyzing a sample, comprising:
   a sample holder into which the sample is placed;
   an oven for heating the sample according to a temperature program characterized by a modulation amplitude, a modulation frequency and an underlying heating rate, wherein the underlying heating rate varies with time;
   a detector for detecting weight information of the sample when it is heated according to the temperature program;
   a computer for determining a kinetic parameter from the weight information; and
   a controller for varying the underlying heating rate in accordance with the determined kinetic parameter.

49. The system recited in claim 48, wherein the weight information comprises one of a weight of the sample, a weight change of the sample and rate of weight change of the sample.

50. The system recited in claim 48, wherein the kinetic parameter is one of an activation energy, a pre-exponential factor and a reaction node.

51. The system recited in claim 48, wherein the kinetic parameter is rate of weight change and the controller varies the underlying heating rate so as to maintain a constant rate of weight change.

52. A method for analyzing a sample, comprising the steps of:
   placing the sample in a sample holder;
   heating the sample according to a temperature program characterized by a modulation amplitude, a modulation frequency and an underlying heating rate, wherein the underlying heating rate varies with time;
   detecting weight information of the sample when it is heated according to the temperature program;
   determining a kinetic parameter from the weight information; and
   varying the underlying heating rate in accordance with the determined kinetic parameter.

53. The method recited in claim 52, wherein the weight information comprises one of a weight of the sample, a weight change of the sample and a rate of weight change of the sample.

54. The method recited in claim 52, wherein the kinetic parameter is one of an activation energy, a pre-exponential factor and a reaction node.

55. The method recited in claim 52, wherein the kinetic parameter is rate of weight change, and wherein said varying step further comprising the step of varying the underlying heating rate so as to maintain a constant rate of weight change.

56. A thermogravimetric analyzer for analyzing a sample, comprising:
   a sample holder into which the sample is placed;
   an oven to heat a sample;
   a computer to control the oven to heat the sample according to a temperature program that can be characterized by a modulation amplitude and a modulation frequency;
   a detector for determining weight information of the sample as the sample is heated according to the temperature program; and
   means for transmitting the weight information to a personal computer that determines a kinetic parameter using the weight information.

57. The thermogravimetric analyzer recited in claim 56, wherein said detector comprises an electrobalance.

58. The thermogravimetric analyzer recited in claim 56, wherein the temperature program can further be characterized as having an underlying heating rate.

59. The thermogravimetric analyzer recited in claim 58, wherein said underlying heating rate is zero.

60. The thermogravimetric analyzer recited in claim 56, further comprising means for using the kinetic parameter to adjust the temperature program.

61. The thermogravimetric analyzer recited in claim 60, wherein said weight information is rate of weight change, and the kinetic parameter is used to adjust the underlying heating rate to provide a constant average rate of weight change.

62. A method for analyzing a sample, comprising the steps of:
   placing the sample in a sample holder;
   heating the sample according to a temperature program that can be characterized by a modulation amplitude and a modulation frequency;
   detecting weight information of the sample as the sample is heated according to the temperature program; and
   transmitting the weight information to a personal computer that determines a kinetic parameter using the weight information.

63. The method recited in claim 62, wherein the detecting step comprises detecting the weight information using an electrobalance.

64. The method recited in claim 62, wherein said heating step further comprising the step of heating the sample according to a temperature program can further be characterized as having an underlying heating rate.

65. The method recited in claim 64, wherein said heating step further comprising the step of heating the sample according to a temperature program said underlying heating rate is zero.

66. The method recited in claim 62, further comprising the step of adjusting the temperature program according to the determined kinetic parameter.

67. The method recited in claim 66, wherein said weight information is rate of weight change, and further comprising the step of adjusting the underlying heating rate to provide a constant average rate of weight change.

68. A system for analyzing a sample, comprising:
   a sample holder into which the sample is placed;
   a temperature program having a plurality of linear segments to heat the sample;
   a detector to determine weight information of the sample as it is heated according to the temperature program; and
   a computer to determine a kinetic parameter based on the weight information.

69. The system recited in claim 68, wherein each linear segments is entered individually.

70. The system recited in claim 68, wherein a repeat unit comprising a first linear segment and a second linear segment is entered as well as a repeat factor indicating the number of times the repeat unit is repeated.

71. The system recited in claim 70, wherein the first linear segment is represented by a heating rate and a duration; and the second linear segment is represented by an isotherm held for a length equal to the duration.

72. The system recited in claim 70, wherein the first linear segment is represented by a heating rate and a heating time and the second segment is represented by a cooling rate and a cooling time.

73. The system recited in claim 70, wherein the first linear segment is represented by a cooling rate and a cooling time and the second segment is represented by a heating rate and a heating time.

74. The system recited in claim 70, wherein the first linear segment is represented by a first temperature, a second temperature and a heating rate from said first temperature to said second temperature and wherein said second linear segment is represented by third temperature and the length of said third segment is such that the time required to change from the second temperature to the third temperature is equal to the time of the first linear segment.

75. A method for analyzing a sample, comprising:
   placing a sample into a sample holder;

creating a temperature program having a plurality of linear segments;

heating the sample according to the temperature program;

determining weight information of the sample as it is heated according to the temperature program; and determining a kinetic parameter based on the weight information.

76. The method recited in claim 75, wherein said creating step comprised the step of entering each linear segment individually.

77. The method recited in claim 75, wherein said creating step comprises the steps of:

defining a repeat unit comprising a first linear segment and a second linear segment; and defining a repeat factor indicating the number of times the repeat unit is repeated.

78. The method recited in claim 77, wherein said step of defining a repeat unit comprises the steps of:

defining the first linear segment by a heating rate and a duration; and defining the second linear segment by an isotherm held for a length equal to the duration.

79. The method recited in claim 77, wherein said step of defining a repeat unit comprises the steps of:

defining the first linear segment by a heating rate and a heating time;

defining the second linear segment by a cooling rate and a cooling time.

80. The method recited in claim 77, wherein said step of defining a repeat unit comprises the steps of:

defining the first linear segment by a cooling rate and a cooling time; and defining the second segment by a heating rate and a heating time.

81. The method recited in claim 77, wherein the step of defining a repeat unit comprises the steps of:

defining the first linear segment by a first temperature, a second temperature and a heating rate from said first temperature to said second temperature; and defining said second linear segment by a third temperature and the length of said third segment is such that the time required to change from the second temperature to the third temperature is equal to the time of the first linear segment.

* * * * *